(12) United States Patent
Bell

(10) Patent No.: US 6,427,467 B1
(45) Date of Patent: Aug. 6, 2002

(54) WATER MIST COOLING SYSTEM

(76) Inventor: Norris A. Bell, 5419 8th Ave., Los Angeles, CA (US) 90043

( * ) Notice: Subject to any disclaimer, the term of this patent is extended or adjusted under 35 U.S.C. 154(b) by 0 days.

(21) Appl. No.: 09/895,240

(22) Filed: Jun. 29, 2001

(51) Int. Cl.[7] .............................................. F25D 23/12
(52) U.S. Cl. ...................... 62/259.3; 2/181.6; 2/182.3; 2/209.13
(58) Field of Search .............................. 62/259.3; 2/181, 2/181.6, 182.3, 209.13

(56) References Cited

U.S. PATENT DOCUMENTS

| 4,586,280 | A | * | 5/1986 | Dane ............................... 2/171 |
| 5,261,399 | A | * | 11/1993 | Klatz et al. .................. 607/104 |
| 5,353,605 | A | * | 10/1994 | Naaman ....................... 2/171.3 |
| 5,410,746 | A | * | 4/1995 | Gelber ......................... 2/209.13 |
| 5,867,999 | A | * | 2/1999 | Bratton et al. ................. 165/46 |
| 5,940,880 | A | * | 8/1999 | Phillips ........................... 2/181 |
| 6,050,099 | A | * | 4/2000 | Lopa et al. .................. 62/259.3 |
| 6,126,680 | A | * | 10/2000 | Wass ........................... 607/107 |

* cited by examiner

*Primary Examiner*—William C. Doerrler
*Assistant Examiner*—Mohammad M Ali

(57) ABSTRACT

A water mist cooling system for providing cooling through evaporation. The water mist cooling system includes a cap member which includes a body portion and a bill portion and is designed for fitting on a human head, a reservoir member coupled to the cap member which is designed for holding water, and a spray assembly coupled to the cap member which is in environmental communication with the reservoir member and is used for dispersing water onto the head and face of the user.

7 Claims, 2 Drawing Sheets

WATER MIST COOLING SYSTEM

BACKGROUND OF THE INVENTION

1. Field of the Invention

The present invention relates to personal cooling devices and more particularly pertains to a new water mist cooling system for providing cooling through evaporation.

2. Description of the Prior Art

The use of personal cooling devices is known in the prior art. More specifically, personal cooling devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,715,533; 4,162,764; 5,197,292; U.S. Pat. No. Des. 397,765; U.S. Pat. Nos. 3,353,749; and 3,352,364.

While these devices fulfill their respective, particular objectives and requirements, the aforementioned patents do not disclose a new water mist cooling system. The inventive device includes a cap member which includes a body portion and a bill portion and is designed for fitting on a human head, a reservoir member coupled to the cap member which is designed for holding water, and a spray assembly coupled to the cap member which is in environmental communication with the reservoir member and is used for dispersing water onto the head and face of the user.

In these respects, the water mist cooling system according to the present invention substantially departs from the conventional concepts and designs of the prior art, and in so doing provides an apparatus primarily developed for the purpose of providing cooling through evaporation.

SUMMARY OF THE INVENTION

In view of the foregoing disadvantages inherent in the known types of personal cooling devices now present in the prior art, the present invention provides a new water mist cooling system construction wherein the same can be utilized for providing cooling through evaporation.

The general purpose of the present invention, which will be described subsequently in greater detail, is to provide a new water mist cooling system apparatus and method which has many of the advantages of the personal cooling devices mentioned heretofore and many novel features that result in a new water mist cooling system which is not anticipated, rendered obvious, suggested, or even implied by any of the prior art personal cooling devices, either alone or in any combination thereof.

To attain this, the present invention generally comprises a cap member which includes a body portion and a bill portion and is designed for fitting on a human head, a reservoir member coupled to the cap member which is designed for holding water, and a spray assembly coupled to the cap member which is in environmental communication with the reservoir member and is used for dispersing water onto the head and face of the user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new water mist cooling system apparatus and method which has many of the advantages of the personal cooling devices mentioned heretofore and many novel features that result in a new water mist cooling system which is not anticipated, rendered obvious, suggested, or even implied by any of the prior art personal cooling devices, either alone or in any combination thereof.

It is another object of the present invention to provide a new water mist cooling system which may be easily and efficiently manufactured and marketed.

It is a further object of the present invention to provide a new water mist cooling system which is of a durable and reliable construction.

An even further object of the present invention is to provide a new water mist cooling system which is susceptible of a low cost of manufacture with regard to both materials and labor, and which accordingly is then susceptible of low prices of sale to the consuming public, thereby making such water mist cooling system economically available to the buying public.

Still yet another object of the present invention is to provide a new water mist cooling system which provides in the apparatuses and methods of the prior art some of the advantages thereof, while simultaneously overcoming some of the disadvantages normally associated therewith.

Still another object of the present invention is to provide a new water mist cooling system for providing cooling through evaporation.

Yet another object of the present invention is to provide a new water mist cooling system which includes a cap member which includes a body portion and a bill portion and is designed for fitting on a human head, a reservoir member coupled to the cap member which is designed for holding water, and a spray assembly coupled to the cap member which is in environmental communication with the reservoir member and is used for dispersing water onto the head and face of the user.

Still yet another object of the present invention is to provide a new water mist cooling system that can be used while performing a variety of outdoor activities.

Even still another object of the present invention is to provide a new water mist cooling system that allows the user to keep their hands free.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
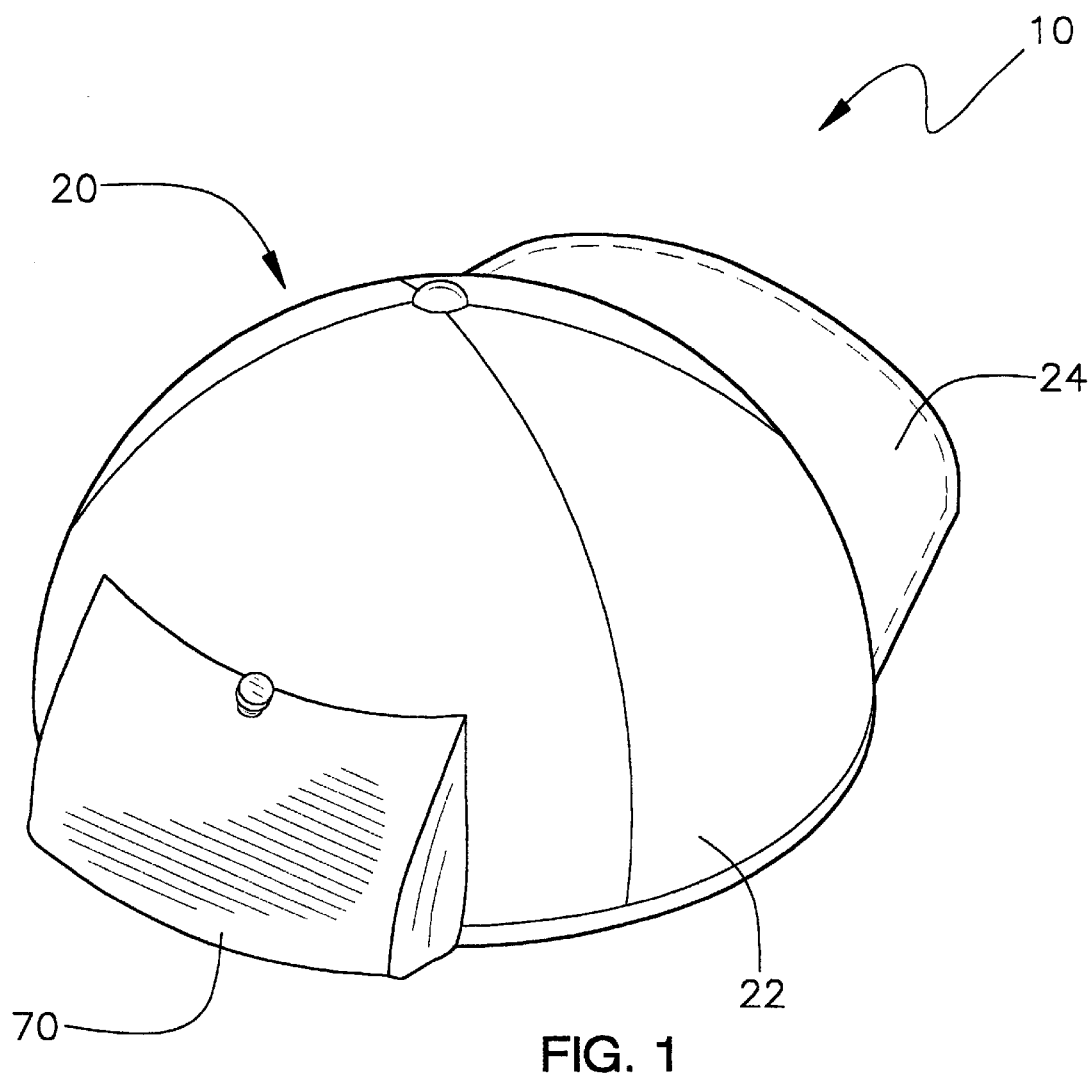
FIG. 1 is a schematic perspective view of a new water mist cooling system according to the present invention.
Figure 2:
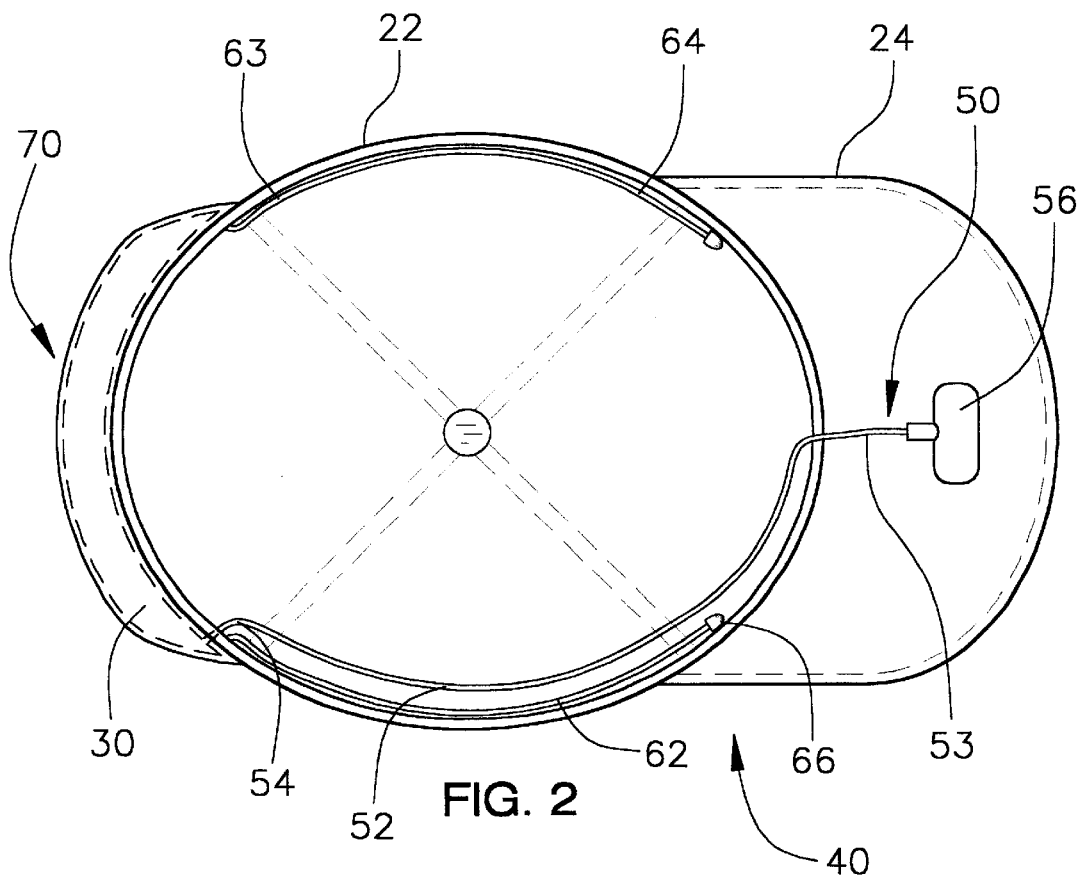
FIG. 2 is a schematic bottom view of the present invention.
Figure 3:
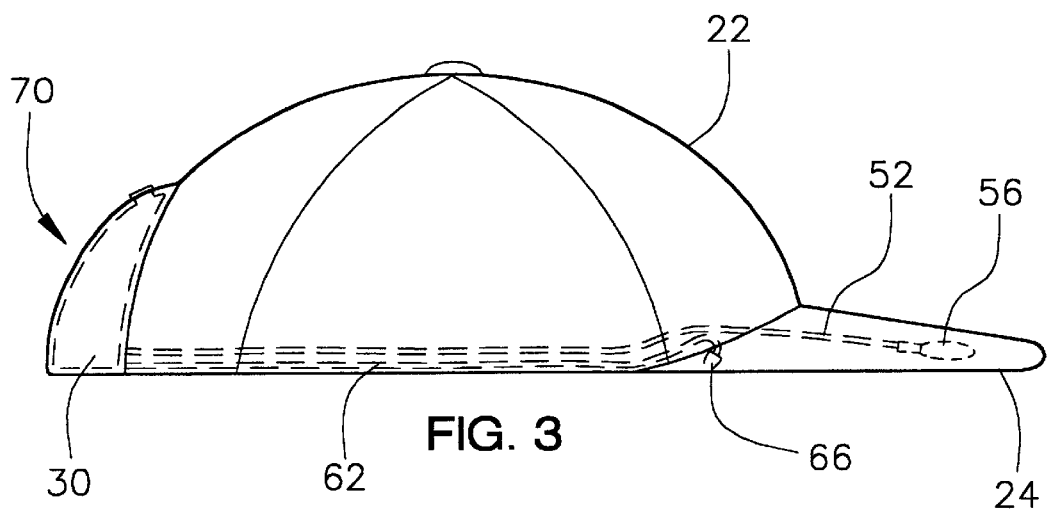
FIG. 3 is a schematic side view of the present invention.

With reference now to the drawings, and in particular to FIGS. 1 through 3 thereof, a new water mist cooling system embodying the principles and concepts of the present invention and generally designated by the reference numeral 10 will be described.

As best illustrated in FIGS. 1 through 3, the water mist cooling system 10 generally comprises a cap member 20, a reservoir member 30, and a spray assembly 40.

The cap member 20 includes a body portion 22 and a bill portion 24. The cap member 20 is designed for fitting on a human head.

The reservoir member 30 is coupled to the cap member 20. The reservoir member 30 is substantially hollow and designed for holding water.

The spray assembly 40 is also coupled to the cap member 20. The spray assembly 40 is in environmental communication with the reservoir member 30. The spray assembly 40 is for dispersing water onto the head and face of the user.

The spray assembly 40 further comprises a pressure subassembly 50 and a distribution subassembly 60. The pressure subassembly 50 is used for urging water to flow from the reservoir member 30. The distribution subassembly 60 is for distributing water flowing from the reservoir member 30 onto the face and head of the user.

The pressure subassembly 50 further comprises a pressure tube 52 and a pressure pump 56. The pressure tube 52 is for directing air into the reservoir member 30 to displace the water. The pressure tube 52 is substantially elongate and hollow. The pressure tube 52 includes a first end 53, which is coupled to the bill portion 24 of the cap member 20. The pressure tube 52 includes a second end 54, which is coupled to the reservoir member 30. The pressure pump 56 is designed for forcing air into the pressure tube 52 when a compressive force is applied to the pressure pump 56. The pressure pump 56 is coupled to the first end 53 of the pressure tube 54. The pressure pump 56 is positioned on an underside of the bill portion 24 of the cap member 20, to facilitate access by the user.

In an embodiment the distribution subassembly 60 further comprises two distribution tubes 62 and two distribution nozzles 66. Each of the distribution tubes 62 is in environmental communication with the reservoir member 30. Each one of the distribution tubes 62 is for routing water forced from the reservoir member 30 by air from the pressure subassembly 50. Each one of the distribution tubes 62 includes a first end 63 coupled to a bottom portion of the reservoir member 30. Each one of the distribution tubes 62 includes a second end 64, which is positioned adjacent to the bill portion 24 for directing water onto the face and head of the user. Each one of the distribution tubes 62 is positioned adjacent to an associated side of the cap member 20. Each of the distribution nozzles 66 is coupled to the second end 64 of and associated one of the distribution tubes 62. The distribution nozzles 66 are for atomizing the water delivered by the distribution tubes 62 for facilitating cooling of the user by evaporation.

In an embodiment a covering member 70 is positioned over the reservoir member 30. The covering member70 is for visually obfuscating the reservoir member 30.

In use, the reservoir member is filled with water. The cap member is worn in the conventional manner. When cooling is desired, the user presses on the pressure pump forcing air into the reservoir member and in turn forcing water our of the reservoir member. The water is conducted along the cap member by the distribution tubes and is atomized by the nozzles to provide a fine mist for cooling the user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A water mist cooling system for personal use comprising:

a cap member having a body portion and a bill portion, said cap member being adapted for fitting on a human head;

a reservoir member coupled to said cap member, said reservoir member being substantially hollow, said reservoir member being adapted for holding water;

a spray assembly coupled to said cap member, said spray assembly being in environmental communication with said reservoir member, said spray assembly being for dispersing water onto the head and face of the user:

a pressure subassembly for urging water to flow from said reservoir member;

a distribution subassembly for distributing water flowing from said reservoir member onto the face and head of the user;

said distribution subassembly having:
a distribution tube in environmental communication with said reservoir member, said distribution tube being for routing water forced from said reservoir member by air from said pressure subassembly, said distribution tube having a first end coupled to a bottom portion of said reservoir member, said distribution tube having a second end positioned adjacent to said bill portion for directing water onto the face and head of the user; and
a distribution nozzle coupled to said second end of said distribution tube, said distribution nozzle being for atomizing the water delivered by said distribution tube for facilitating cooling of the user by evaporation.

2. The water mist cooling system of claim 1, wherein said pressure subassembly further comprises a pressure tube for directing air into said reservoir member to displace the water, said pressure tube being substantially elongate, said pressure tube being substantially hollow, said pressure tube having a first end coupled to said bill portion of said cap member, said pressure tube having a second end coupled to said reservoir member.

3. The water mist cooling system of claim 2, wherein said pressure subassembly further comprises a pressure pump adapted for forcing air into said pressure tube when a compressive force is applied to said pressure pump, said pressure pump being positioned un an underside of said bill portion of said cap member to facilitate access by the user.

4. The water mist cooling system of claim 1, wherein said distribution subassembly further comprises two distribution tubes in environmental communication with said reservoir member, each one of said distribution tubes being for routing water forced from said reservoir member by air from said pressure subassembly, each one of said distribution tubes having a first end coupled to a bottom portion of said reservoir member, each one of said distribution tubes having a second end positioned adjacent to said bill portion for directing water onto the face and head of the user, each one of said distribution tubes being positioned adjacent to an associated side of said cap member.

5. The water mist cooling system of claim 4 wherein said distribution subassembly further comprises a pair of distribution nozzles, each distribution nozzle being coupled to said second end of and associated one of said distribution tubes, said distribution nozzles being for atomizing the water delivered by said distribution tubes for facilitating cooling of the user by evaporation.

6. A water mist cooling system for personal use comprising:
a cap member having a body portion and a bill portion, said cap member being adapted for fitting on a human head;
a reservoir member coupled to said cap member, said reservoir member being substantially hollow, said reservoir member being adapted for holding water;
a spray assembly coupled to said cap member, said spray assembly being in environmental communication with said reservoir member, said spray assembly being for dispersing water onto the head and face of the user:
a pressure subassembly for urging water to flow from said reservoir member;
a distribution subassembly for distributing water flowing from said reservoir member onto the face and head of the user; and
a covering member positioned over said reservoir member, said covering member being for visually obfuscating said reservoir member.

7. A water mist cooling system for personal use comprising:
a cap member having a body portion and a bill portion, said cap member being adapted for fitting on a human head;
a reservoir member coupled to said cap member, said reservoir member being substantially hollow, said reservoir member being adapted for holding water;
a spray assembly coupled to said cap member, said spray assembly being in environmental communication with said reservoir member, said spray assembly being for dispersing water onto the head and face of the user;
said spray assembly further comprises:
a pressure subassembly for urging water to flow from said reservoir member;
a distribution subassembly for distributing water flowing from said reservoir member onto the face and head of the user;
said pressure subassembly further comprises
a pressure tube for directing air into said reservoir member to displace the water, said pressure tube being substantially elongate, said pressure tube being substantially hollow, said pressure tube having a first end coupled to said bill portion of said cap member, said pressure tube having a second end coupled to said reservoir member;
a pressure pump adapted for forcing air into said pressure tube when a compressive force is applied to said pressure pump, said pressure pump being positioned un an underside of said bill portion of said cap member to facilitate access by the user;
wherein said distribution subassembly further comprises two distribution tubes in environmental communication with said reservoir member, each one of said distribution tubes being for routing water forced from said reservoir member by air from said pressure subassembly, each one of said distribution tubes having a first end coupled to a bottom portion of said reservoir member, each one of said distribution tubes having a second end positioned adjacent to said bill portion for directing water onto the face and head of the user, each one of said distribution tubes being positioned adjacent to an associated side of said cap member;
a pair of distribution nozzles, each distribution nozzle being coupled to said second end of and associated one of said distribution tubes, said distribution nozzles being for atomizing the water delivered by said distribution tubes for facilitating cooling of the user by evaporation; and
a covering member positioned over said reservoir member, said covering member being for visually obfuscating said reservoir member.

* * * * *